United States Patent [19]

Takekawa

[11] Patent Number: 4,457,893
[45] Date of Patent: Jul. 3, 1984

[54] AUTOMATED APPARATUS FOR PHOTOMETRICALLY DETECTING IMMUNOLOGICAL AGGLUTINATING REACTIONS

[75] Inventor: Hiroshi Takekawa, Kunitachi, Japan

[73] Assignee: Olympus Optical Co. Ltd., Japan

[21] Appl. No.: 398,870

[22] Filed: Jul. 16, 1982

Related U.S. Application Data

[62] Division of Ser. No. 184,057, Aug. 28, 1980.

[30] Foreign Application Priority Data

Sep. 10, 1979 [JP] Japan .................. 54-115103

[51] Int. Cl.³ .................. G01N 33/54; G01N 35/02; G01N 35/06
[52] U.S. Cl. .................. 422/64; 364/497; 422/67; 422/68; 436/808
[58] Field of Search .................. 422/56, 64, 67, 68; 436/808; 364/497

[56] References Cited

U.S. PATENT DOCUMENTS

| | | |
|---|---|---|
| 3,562,384 | 2/1971 | Arquilla . |
| 3,883,308 | 5/1975 | Matte . |
| 4,118,192 | 10/1978 | Sawai . |
| 4,148,607 | 4/1979 | Bernoco . |
| 4,205,954 | 6/1980 | Babson . |
| 4,234,539 | 11/1980 | Ginsberg . |
| 4,276,051 | 6/1981 | Ginsberg .................. 364/497 X |
| 4,311,394 | 1/1982 | Manabe .................. 422/64 X |
| 4,313,735 | 2/1982 | Yamashita .................. 422/64 X |
| 4,338,279 | 7/1982 | Orimo .................. 422/64 X |
| 4,346,056 | 8/1982 | Sakurada .................. 422/64 |

FOREIGN PATENT DOCUMENTS 1539674 9/1968 France .

OTHER PUBLICATIONS

G. C. Webster, Biochimica et Biophysica and Acta, 207(1), 371-373 (1970).
Albert L. Lehninger, "Biochemistry", 2nd Ed., p. 66, Worth Publishers, New York, 1978.
I. M. Kolthoff et al., "Textbook of Quant. Inorg. Analysis", p. 418, MacMillan Co., New York 1947.

*Primary Examiner*—Sidney Marantz
*Attorney, Agent, or Firm*—Parkhurst & Oliff

[57] ABSTRACT

Method and apparatus for detecting immunological agglutinating reaction comprises steps of measuring light absorptions of a liquid medium with antibody before and after antigen-antibody reaction by using a light which is absorbable by the antibody, and calculating the difference of the light absorptions, for determining the presence or absence of the agglutination based on the fact that the agglutinating reaction reduces the concentration of the antibody affecting the light absorption of the liquid medium. The apparatus includes a turntable, two photometers, sample and reagent handling means and calculator.

8 Claims, 3 Drawing Figures

AUTOMATED APPARATUS FOR PHOTOMETRICALLY DETECTING IMMUNOLOGICAL AGGLUTINATING REACTIONS

This is a division of application Ser. No. 184,057 filed Aug. 28, 1980.

BACKGROUND OF THE INVENTION

1. Field of the Invention

This invention relates to a method of detecting immunological agglutinating reaction.

2. Description of the Prior Art

As an example of the prior art method of determining blood group, the method disclosed by U.S. Pat. No. 3,883,308 granted to Claude Matte (to be referred to as "Matte", hereinafter) will be briefly reviewed. The method of Matte comprises steps of pouring certain amount of a centrifugated suspension having 2 to 5% of blood corpuscles to be analyzed and a specific antiserum into a reaction vessel having a curved bottom of brandy glass shape, agitating the suspension and the antiserum, keeping the reaction vessel standstill, effecting centrifugal precipitation, applying a special high-speed shake-up to the reaction vessel so as to disperse the precipitated blood corpuscles, agitating the reaction vessel comparatively slowly so as to collect agglutinates at the central portion of the bottom of the reaction vessel for producing an agglutinates pattern at the bottom of the reaction vessel, and detecting the agglutinates pattern by photometry. This method is based on a phenomenon that, after the aforementioned shake-up and comparatively slow agitation, particles combined by agglutination are quickly collected at the central portion of the reaction vessel while non-agglutinated particles are dispersed again in the suspension and not collected at the central portion of the reaction vessel. To detect the agglutinates pattern formed at the central portion of the bottom of the reaction vessel, a photoelectric measurement such as nephelometry or opacimetry is used; namely, when luminous flux passes through the suspension, the degree of light absorption by the suspension varies depending on the density of the blood corpuscles suspended between the top surface of the suspension and the bottom of the reaction vessel, which variation of the light absorption is photoelectrically measured as different degrees of turbidity. More particularly, in the example of FIG. 33 of Matte, luminous flux is directed from above to the reaction vessel having a transparent bottom of brandy glass shape, and a mask plate or a bottom plate having a central aperture and an annular aperture around the central aperture is disposed below the reaction vessel in such a manner that, light coming through the central aperture is applied to a first light-receiving element while light coming through the annular aperture is applied to a second light-receiving element through a lens. Thus, the amount of light incident to the first light-receiving element after passing through the central portion of the reaction vessel represents the turbidity at the central portion of the suspension being analyzed, while the amount of light incident to the second light-receiving element after passing through the peripheral portion of the reaction vessel represents the turbidity at the peripheral portion of the suspension being analyzed. Accordingly, if the amount of light of the light passing through the central portion of the suspension being analyzed decreases as compared with its reference value and at the same time the amount of light of the light passing through the peripheral portion of the suspension increases as compared with its reference value, "presence of agglutination" is determined. On the other hand, if the amounts of light of the lights passing through the central portion and the peripheral portion of the suspension being analyzed remain unchanged as compared with their reference values, "absence of agglutination" is determined.

The conventional method of detecting and determining the agglutinates pattern, as exemplified by Matte, has a number of shortcomings. Namely, the reference values of the amounts of light for the first and second light-receiving elements must be calibrated and set beforehand, by using a suitable reference agglutinates pattern, which calibration and setting tend to make the operation of the determination cumbersome. Besides, the reference agglutinates pattern is not necessarily identical with actual agglutinates patterns of the suspensions to be analyzed, so that the deviation of the reference agglutinates pattern from the actual agglutinates patterns tends to cause an error in determination of the presence or absence of agglutination. Moreover, the conventional method requires to prevent that part of the luminous flux incident to the peripheral portion of the suspension which is scattered by particles therein from reaching the first light-receiving element through the central aperture of the mask or bottom plate, and to prevent that part of the luminous flux incident to the central portion of the suspension which is scattered by particles therein from reaching the second light-receiving element through the annular aperture of the mask or the bottom plate. Accordingly, the mask or bottom plate and the first and second light-receiving elements must be so constructed and disposed as to meet the aforementioned requirements, which construction and disposition tend to make the optical system for detecting the light absorption complicated and difficult to manufacture.

SUMMARY OF THE INVENTION

Therefore, an object of the present invention is to obviate the aforementioned shortcomings of the prior art, by providing a method of detecting immunological agglutinating reaction which enables easy and accurate detection of immunological agglutinating reaction by an easily operable apparatus of simple construction.

According to the present invention, there is provided a method of detecting an immunological agglutinating reaction in carrying out immunological analysis based on antigen-antibody reaction between antigen particles and a liquid medium having antibody to be measured, characterized by comprising steps of pouring said liquid medium into a reaction vessel, effecting a first light absorption measurement on said liquid medium by using a light whose wavelength is suitable for selective absorption by the antibody in the liquid medium, pouring said antigen particles into said reaction vessel containing said liquid medium for causing said antigen-antibody reaction, effecting a second light absorption measurement on a supernatant fluid after said antigen-antibody reaction by using a light having the same wavelength as that for said first light absorption measurement, and determining difference between light absorptions obtained by said first and second light absorption measurements.

In immunological, especially serological, agglutinating reactions, antigens partcipating in the reactions are generally immune globulins such as $I_gG, I_gM$, and $I_gA$, which are protein. It is known that protein has a strong light-absorbing property for lights of wavelengths 190 nm and 280 nm. In the present invention, the light absorptions of both the liquid medium having antibody to be measured and the supernatant fluid after the antigen-antibody reaction are measured by using a light whose wavelength is suitable for selective absorption by the antibody, so that the agglutinating reaction is detected based on the difference between the two light absorptions. Thus, the method of the present invention does not effect the direct detection of the agglutinates pattern which is necessary in the prior art, so that the present invention simplifies the optical system for photometry and eliminates the use of any reference agglutinates pattern. Accordingly, the operation for carrying out the method of the present invention is simple. It is noted that in the Matte method the reaction vessel is strongly shaken after centrifugation for dispersing the precipitated particles from the bottom of the reaction vessel, but the antigen-antibody reaction in the method of the present invention can be carried out simply by using a widely utilized centrifuge or by keeping the reaction vessel standstill. Consequently, the present invention simplifies the analyzing process for detecting immunological agglutinating reaction, and the method of the present invention can be carried out easily by using an apparatus of simple mechanism.

BRIEF DESCRIPTION OF THE DRAWINGS

For a better understanding of the invention, reference is made to the accompanying drawings, in which.

Like parts are designated by like numerals and symbols throughout different views of the drawings.

DETAILED DESCRIPTION OF THE PREFERRED EMBODIMENTS

Figure 1:
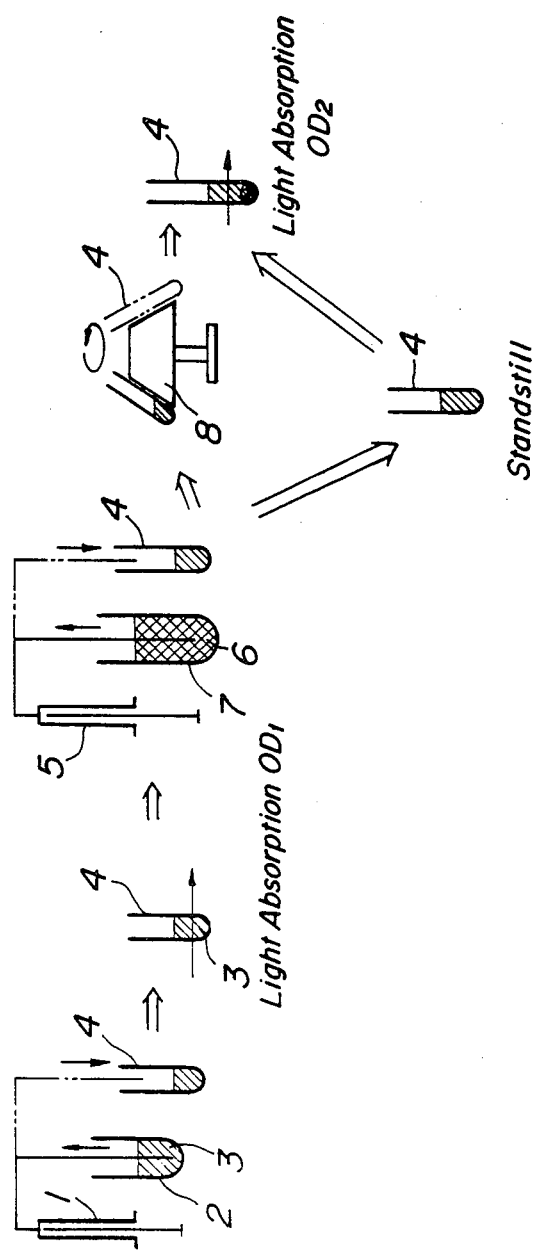
FIG. 1 is a diagrammatic illustration of different steps to be successvely effected by a method according to the present invention.

Referring to FIG. 1 showing successive steps of the method of the present invention, a syringe 1 is connected to a serum container 2 and acts to take a certain amount of serum 3 from the container 2 for pouring it into a reaction vessel 4. In the illustrated example, the reaction vessel 4 is a transparent test tube, but the present invention is not restricted to such test tube. Light absorption $OD_1$ of the thus poured serum 3 is measured through the wall of the reaction vessel 4 by using, for instance, a light with a wavelength of 280 nm. The reaction vessel 4 is made of a material which has a high transparency to the light of the wavelength used, preferably quartz for the light with the 280 nm wavelength.

After the light absorption measurement on the serum, another syringe 5 takes a solution 6 containing antigen particles such as erythrocytes (to be referred to as "antigen solution", hereinafter) from a container 7, for pouring a certain amount of the antigen solution 6 into the reaction vessel 4 carrying the serum 3. Whereby, agglutinating reaction between antigen and antibody occurs, for causing precipitations of antigen particles or agglutinates. The agglutinating reaction can be effected either by using a centrifuge 8 or by keeping the reaction vessel 4 standstill, as pointed out in the foregoing. After completion of the antigen-antibody reaction, light absorption $OD_2$ of a supernatant fluid of the serum after the reaction is measured by using the light of 280 nm wavelength as in the case of the measurement of the aforementioned light absorption $OD_1$. Then, the difference between the values of the light absorptions $OD_1$ and $OD_2$ thus measured are determined, for detecting the agglutinating reaction based on the difference.

It is noted here that the antigen particles sediment to the bottom of the reaction vessel 4 because the antigen particles have a larger specific gravity than that of the serum component, regardless of whether the antigen-antibody reaction is of agglutinating type or non-agglutinating type. In the case of the agglutinating type antigen-antibody reaction, the immune globulins as the antibody are adsorbed by the antigen particles, so as to sediment together with the antigen particles, so that the concentration of protein in the serum forming the supernatant fluid decreases accordingly. Whereby, a difference is generated between the light absorptions $OD_1$ and $OD_2$, for allowing the determination of the "presence of agglutination". On the other hand, in the case of non-agglutinating type antigen-antibody reaction, the immune globulins are not adsorbed by the sedimenting antigen particles, so that the concentration of protein in the serum forming the supernatant fluid is not changed. Accordingly, the two light absorptions $OD_1$ and $OD_2$ are the same, and the "absence of agglutination" can be determined.

The amount of the antibody to be adsorbed by the antigen particles varies depending on the amount of the antigen particles and the strength of the antibody, so that the amount of the residual immune globulins in the serum forming the supernatant fluid varies accordingly. In view of this variation of the absorption of antibody, the calculation of the difference between the two light absorptions $OD_1$ and $OD_2$ allows the determination of the degree of agglutination and the quantitative analysis thereof; namely, the quantitative analyses of the antigen and the antibody adsorbed by the antigen.

Figure 2:
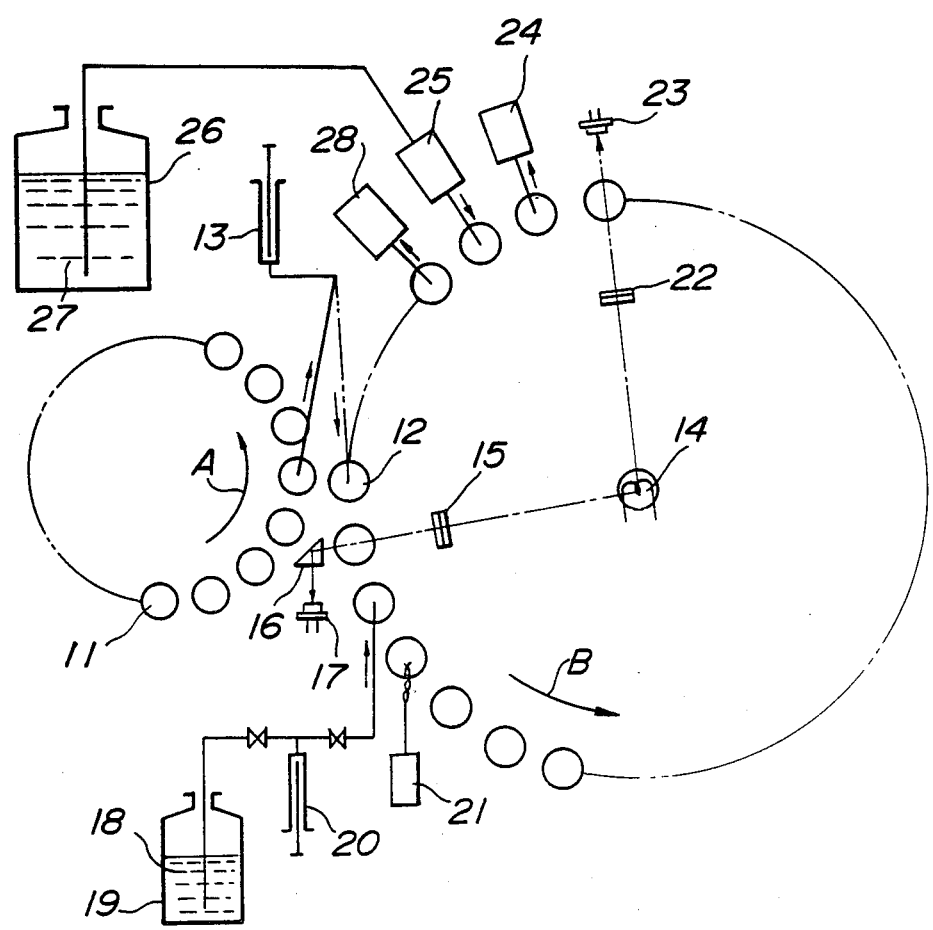
FIG. 2 is a schematic illustration of an example of devices for effecting the method according to the present invention.

FIG. 2 schematically illustrates an example of possible detecting devices for carrying out the method according to the present invention. The example of FIG. 2 is for analyzing samples consisting of serums, and a plurality of serums to be analyzed are placed in corresponding sample cups 11, which cups are intermittently forwarded in succession in the direction of the arrow A of the figure. A series of reaction vessels 12 are also intermittently forwarded in succession in the direction of the arrow B of the figure with the same period as that of the sample cups 11. A sample syringe 13 sucks a predetermined amount of the sample serum from the sample cup 11 at a sucking position and pours the sample serum thus sucked into the reaction vessel 12 at a pouring position. Thus, the sample serums are transferred from the sample cups 11 to the corresponding reaction vessels 12 in succession. After receiving the sample serum, the reaction vessel 12 comes to a first photometering position, where the light absorption $OD_1$ of the sample serum in the reaction vessel 12 is measured and stored in a suitable memory (not shown). In the example of FIG. 2, a photometric means for measuring the first light absorption $OD_1$ includes a multi-color light source 14, an interference filter 15 for extracting the light with the 280 nm wavelength from the light emitted by the light source 14, the light from the interference filter 15 being directed to the sample serum in the reaction vessel 12 at the first photometering position, and a prism 16 diffracting the light from the reaction vessel 12 toward a light-receiving element 17. The light absorption $OD_1$ of the sample serum is determined on the basis of the output from the light-receiving element 17 and stored in a memory (not shown).

After the measurement of the light absorption at the first photometering position, the reaction vessel 12 comes to a reagent pouring position, where a predetermined amount an antigen solution 18 (for instance, a suspension of blood corpuscles) in a reagent container 19 is poured into the reaction vessel 12 by a reagent syringe 20. The antigen solution is a reagent for effecting the antigen-antibody reaction. When the reaction vessel 12 is forwarded by a predetermined number of steps from the reagent pouring position, an agitator 21 is extended into the reaction vessel 12 for agitating and mixing the sample serum and the reagent in the reaction vessel 12. The antigen-antibody reaction takes place during the time period until the reaction vessel 12 arrives at a second photometering position, where the light absorption $OD_2$ of a supernatant fluid after the antigen-antibody reaction is measured. In the example of FIG. 2, the photometric means at the second photometering position is similar to that at the first photometering position, and the multi-color light source 14 is used in common for both the first and the second photometering positions. At the second photometering position, an interference filter 22 receives the light from the light source 14 and delivers the light with the 280 nm wavelength to the supernatant fluid through the wall of the reaction vessel 12, and the light-receiving element 23 receives the light from the reaction vessel 12 for determining the light absorption $OD_2$ of the supernatant fluid.

The light absorption $OD_2$ of the supernatant fluid thus determined is applied to one input of a differential amplifier (not shown), which differential amplifier has another input for receiving the light absorption $OD_1$ of the corresponding sample serum as measured at the first photometering position and as stored in the memory (not shown), so that the differential amplifier can produce an output signal representing the difference between the two light absorptions $OD_1$ and $OD_2$, for enabling the determination of presence or absence of agglutination. In the case of the presence of agglutination, it is also possible to determine the degree of agglutination and to effect the quantitative analyses of the antigen and the antibody.

After the second photometering position for measuring the light absorption of the supernatant fluid, the reaction vessel 12 comes to a draining position, where the liquid in the reaction vessel 12 is drained by a draining pump 24 and discarded. At the next position, a rinsing pump 25 pours a rinsing fluid 27 (for instance, physiological saline solution) from a container 26 therefor, which rinsing fluid 27 is drained and discarded at the next position of the reaction vessel 12 by another draining pump 28. Whereby, the reaction vessel 12 is cleansed and readied for the next analyzing cycle.

Figure 3:
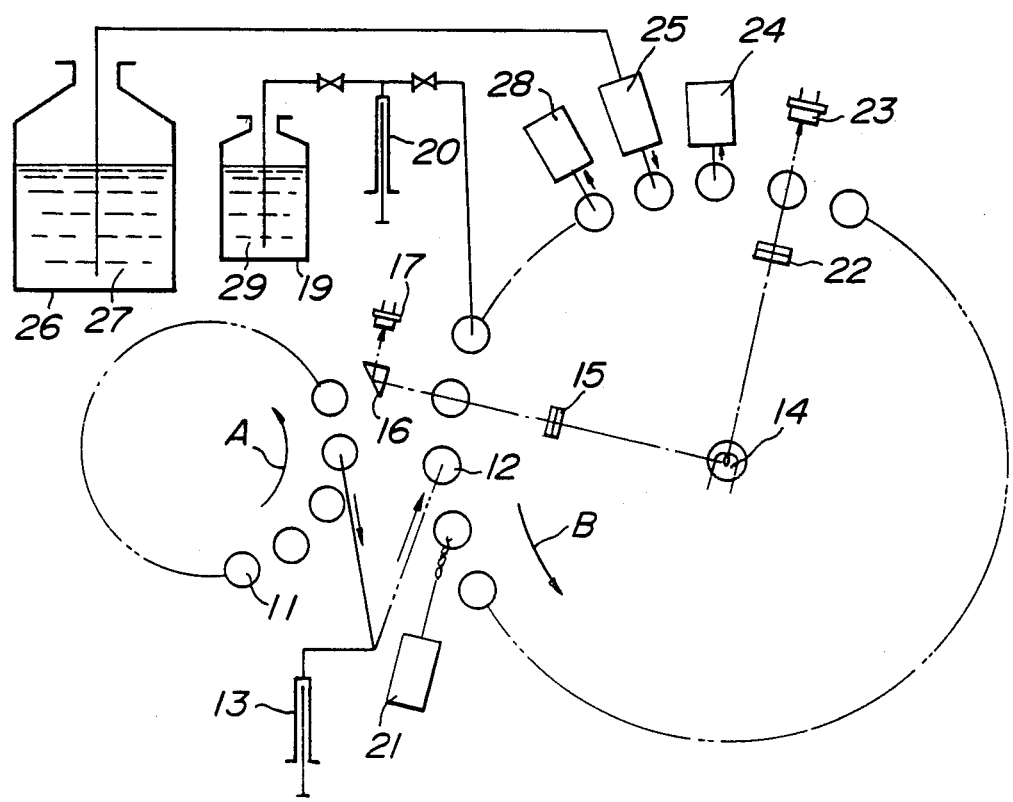
FIG. 3 is a schematic illustration of another example of devices for effecting the method according to the present invention.

FIG. 3 schematically illustrates another example of devices for carrying out the method of the present invention. The example of FIG. 3 is suitable for the case in which samples are antigen solutions (for instance, suspensions of blood corpuscles). Referring to FIG. 3, a fixed amount of a reagent made of a serum containing antibody 29 (serum reagent) is poured into a reaction vessel 12 from a reagent container 19 by a reagent syringe 20. When the reaction vessel 12 arrives at a first photometering position, the light absorption $OD_1$ of the serum reagent is measured. Then, as the reaction vessel 12 arrives at a sample pouring position, a sample pouring syringe 13 pours a predetermined amount of each sample into the reaction vessel 12. Those portions of the example of FIG. 3 which follow the sample pouring position are formed and operated in the same manner as the corresponding portions of the preceding example that has been described in detail hereinbefore by referring to FIG. 2, so that details of those portions which are the same as the corresponding portions of the preceding example will not be described here.

As described in the foregoing, according to the present invention, the light absorptions of both a serum and a supernatant fluid after the antigen-antibody reaction are measured by using a light having a wavelength to be selectively absorbed by antibody, so that the difference of the two light absorptions thus measured provides a basis not only for detection of the presence or absence of agglutinating reaction but also for determination of the degree of agglutination and for quantitative analyses of the antigen and the antibody. The method of the present invention eliminates the need of the direct detection of agglutinates pattern which has been necessary in the prior art, so that optical system of photometry is simplified by the present invention. Besides, calibration and setting of photometric means by using a reference agglutinates pattern are eliminated by the method of the present invention, so that the operation for detecting the agglutinating reaction is also simplified. Moreover, in the method according to the present invention, the special shake-up of the reaction vessel in the Matte method for dispersing the precipitated particles after centrifugation is completely removed. With the method of the present invention, the antigen-antibody reaction can be carried out either by using a widely utilized centrifuge or by keeping the reaction vessel standstill. In short, the method of the present invention is simple, and a device for carrying out the method of the present invention can be easily constructed with a simple mechanism, for instance, by modifying a conventional biochemical analyzing equipment to a certain extent.

Although the present invention has been described with a certain degree of particularity, it is understood that the present disclosure has been made only by way of example and that numerous changes in details of construction and the combination and arrangement of parts may be resorted to without departing from the scope of the invention as hereinafter claimed.

What is claimed is:

1. An apparatus for effecting an immunological analysis based on a reaction between an antibody and an antigen specific to said antibody comprising:

a turntable intermittently rotated in a horizontal plane about a center axis in a given direction and having a plurality of reaction vessel holding portions arranged equidistantly along a periphery of the turntable;

means for pouring a given amount of sample containing antibody or antigen to be analyzed into a reaction vessel indexed at a sample delivery position;

a light source arranged in said center axis of the turntable for horizontally emitting light having a wavelength selectively absorbed by said antibody or antigen in the sample;

first photometric means arranged to receive the light emitted from said light source and transmitted through the reaction vessel containing the sample and indexed at a first photometry position which is downstream with respect to said sample delivery position viewed in the rotational direction of the turntable, said first photometric means measuring a first absorption value of the sample contained in the relevant reaction vessel;

means for pouring a given amount of reagent containing antigen- or antibody-sensitized particles into the reaction vessel indexed at a reagent delivery position which is downstream with respect to said first photometry position viewed in the rotational direction of the turntable to form a test liquid in the relevant reaction vessel;

means for transporting said reaction vessel from said first photometry position to a second photometry position in a substantially standstill manner so that the test liquid separates into supernatant and sediment;

second photometric means arranged to receive the light emitted from said light source and transmitted through a supernatant of the test liquid contained in the reaction vessel indexed at a second photometry position which is downstream with respect to said reagent delivery position viewed in the rotational direction of the turntable, said second photometric means measuring a second absorption value of a supernatant of the test liquid contained in the relevant reaction vessel and not of the sediment;

means for washing the reaction vessel indexed at a washing position which is downstream with respect to said second photometry position; and calculating means for receiving said first and second absorption values measured by said first and second photometric means, to derive a difference therebetween which represents an analytic result of the antibody or antigen contained in the sample;

whereby said sample and reagent pouring means, first and second photometric means, and calculating means are actuated for each step of the intermittent rotation of the turntable to effect immunological analysis for successive samples.

2. An apparatus according to claim 1, wherein said sample delivery position, the first photometry position and the reagent delivery position are arranged adjacently to each other, and said second photometry position is arranged far away from the reagent delivery position.

3. An apparatus according to claim 2, wherein said washing position is arranged adjacent to said second photometry position.

4. An apparatus according to claim 3, wherein said washing position has a range including a plurality of successive stop positions of the turntable.

5. An apparatus for effecting an immunological analysis based on a reaction between an antibody and an antigen specific to said antibody comprising:

a turntable intermittently rotated in a horizontal plane about a center axis in a given direction and having a plurality of reaction vessel holding portions arranged equidistantly along a periphery of the turntable;

means for pouring a given amount of reagent containing antibody or antigen into a reaction vessel indexed at a reagent delivery position;

a light source arranged in said center axis of the turntable for horizontally emitting light having a wavelength selectively absorbed by said antibody or antigen in the reagent;

a first photometric means arranged to receive the light emitted from said light source and transmitted through the reaction vessel containing the reagent and indexed at a first photometry position which is downstream with respect to said reagent delivery position viewed in the rotational direction of the turntable, said first photometric means measuring a first absorption value of the reagent contained in the relevant reaction vessel;

means for pouring a given amount of sample containing antigen- or antibody-sensitized particles to be analyzed into the reaction vessel indexed at a reagent delivery position which is downstream with respect to said first photometry position viewed in the rotational direction of the turntable to form a test liquid in the relevant reaction vessel;

means for transporting said reaction vessel from said first photometry position to a second photometry position in a substantially standstill manner so that the test liquid separates into supernatant and sediment;

second photometric means arranged to receive the light emitted from said light source and transmitted through a supernatant of the test liquid contained in the reaction vessel indexed at a second photometric position which is downstream with respect to the sample delivery position viewed in the rotational direction of the turntable, said second photometric means measuring a second absorption value of the supernatant of the test liquid in the reaction vessel and not the sediment;

means for washing the reaction vessel indexed at a washing position which is downstream with respect to said second photometry position; and calculating means for receiving said first and second absorption values measured by said first and second photometric means to derive a difference therebetween which represents an analytic result of the antigen- or antibody-sensitized particles contained in the sample;

whereby said sample and reagent pouring means, first and second photometric means, and calculating means are actuated for each step of the intermittent rotation of the turntable to effect immunological analysis for successive samples.

6. An apparatus according to claim 5, wherein said reagent delivery position, the first photometry position and sample delivery position are arranged adjacent to each other and said second photometry position is arranged far away from the sample delivery position.

7. An apparatus according to claim 6, wherein said washing position is arranged adjacent to said second photometry position.

8. An apparatus according to claim 7, wherein said washing position has a range including a plurality of successive stop positions of the turntable.

* * * * *